United States Patent [19]

Tamura et al.

[11] Patent Number: 5,776,779
[45] Date of Patent: Jul. 7, 1998

[54] INTEGRAL MULTI-LAYER ELEMENT FOR ANALYZING BILE ACID SULFATE

[75] Inventors: Hiroshi Tamura; Satoshi Chosa; Satoshi Yonehara, all of Kyoto, Japan

[73] Assignee: Kyoto Daiichi Kagaku Co., Ltd., Kyoto, Japan

[21] Appl. No.: 809,108

[22] PCT Filed: Sep. 12, 1995

[86] PCT No.: PCT/JP95/01808

§ 371 Date: Mar. 13, 1997

§ 102(e) Date: Mar. 13, 1997

[87] PCT Pub. No.: WO96/08581

PCT Pub. Date: Mar. 21, 1996

[30] Foreign Application Priority Data

Sep. 13, 1994 [JP] Japan .................................. 6-218662
Sep. 27, 1994 [JP] Japan .................................. 6-231111

[51] Int. Cl.⁶ .................................................. G01N 33/72
[52] U.S. Cl. ................................ 436/56; 422/61; 436/97; 436/170
[58] Field of Search ...................... 422/56–58, 61; 436/96–97, 170

[56] References Cited

FOREIGN PATENT DOCUMENTS 2-145183  4/1990  Japan .
3-224498  3/1991  Japan .

OTHER PUBLICATIONS

Caplus 1991:78186 includes a characterization of the abstract from JP 89-17564.

*Primary Examiner*—Lyle A. Alexander
*Attorney, Agent, or Firm*—Birch, Stewart, Kolasch & Birch, LLP

[57] ABSTRACT

An integral multi-layer analytical element for analyzing bile acid sulfate comprising a support member, a reagent layer on said support member and a porous developing layer on said reagent layer, at least one of the reagent layer and developing layer containing bile acid sulfate sulfatase, 3β-hydroxysteroid dehydrogenase and a combination of thio-$NAD^+$ and reduced NAD or reduced NADP, in which the reagent layer contains a water-soluble polymer, a buffer and at least one component selected from the group consisting of sugar alcohols and $Mn^{2+}$, which element suppresses the increase of blank values and prevents agglomeration of the enzyme during the preparation of a solution for forming the reagent layer.

5 Claims, 1 Drawing Sheet

INTEGRAL MULTI-LAYER ELEMENT FOR ANALYZING BILE ACID SULFATE

BACKGROUND OF THE INVENTION

1. Field of the Invention

The present invention relates to an integral multi-layer element for analyzing bile acid sulfate contained in aqueous liquid samples. In particular, the present invention relates to an integral multi-layer element for quantitatively analyzing bile acid sulfate in aqueous liquid samples, for example, body fluids such as blood (whole blood, blood plasma and serum), cerebrospinal fluid, lymph, saliva, urine, and the like, which element can operate in a dry state and is advantageous in clinical use.

2. Description of the Related Art

JP-A-2-145183 discloses as an analytical method for bile acid sulfate, a solution method comprising converting bile acid sulfate to 3β-hydroxybile acid with bile acid sulfate sulfatase (hereinafter referred to as "BSS"), reacting 3β-hydroxybile acid with 3β-hydroxysteroid dehydrogenase (hereinafter referred to as "3β-HSD") and nicotinamide adenine nucleotides (hereinafter referred to as "NADs") or nicotinamide adenine nucleotide phosphates (hereinafter referred to as "NADPs") as coenzymes, and measuring the amount of NADHs (reduced NADs) or NADPHs (reduced NADPs) which is formed in proportional to the amount of bile acid sulfate.

However, this method has a drawback that an amount of developed color is insufficient for being used in dry analysis since it uses tetrazolium salts in a color-developing system.

A highly sensitive method for analyzing bile acid uses enzymatic cycling (see JP-A-3-224498). This method enables the highly sensitive quantitative analysis of a-type bile acid using α-HSD in the liquid system.

It has been found that it is possible to detect color development of thio-NADH with a relatively simple agent composition when the above two methods are combined and 3β-hydroxybile acid, which has been desulfated with BSS, as the substrate is quantitatively measured with 3β-HSD.

However, the analysis in a liquid system is troublesome, and therefore, it has been desired to develop a dry type integral multi-layer analytical element which is simple and has high sensitivity.

When dry type integral multi-layer analytical elements which use the enzymatic cycling method are produced simply by the conventional methods for producing the dry type test elements, the following problems arise:

(1) A sufficient measuring range is not attained since background color develops in the production process, which may be due to color development of reduced thio-NAD (thio-NADH).

(2) The desulfatase makes a solution turbid in the preparation step of the solution and cannot be dispersed homogeneously in the solution. Therefore, no homogeneous solution is obtained, and measurement errors may arise.

(3) When samples are urine, pH of urine varies with individuals and spreads in a wide range between 4 and 9. However, it is difficult to find a buffer which can buffer the samples in this wide pH range and can be used in a dry system.

Therefore, it has been difficult to apply the agent system for the above solution method in the dry analytical element with maintaining the highly sensitive quantitative analyzing properties of the enzymatic cycling.

The present invention intend to enable the production of an integral multi-layer element for quantitatively analyzing bile acid sulfate with a high sensitivity.

SUMMARY OF THE INVENTION

Accordingly, the present invention provides an integral multi-layer analytical element for analyzing bile acid sulfate comprising a support member, a reagent layer on said support member and a porous developing layer on said reagent layer, at least one of said reagent layer and said developing layer containing bile acid sulfate sulfatase, 3β-hydroxysteroid dehydrogenase and a combination of thio-NAD$^+$ and reduced NADs or reduced NADPs, wherein said reagent layer contains a water-soluble polymer, a buffer and at least one component selected from the group consisting of sugar alcohols and $Mn^{2+}$.

DETAILED DESCRIPTION OF THE INVENTION

Figure 1:
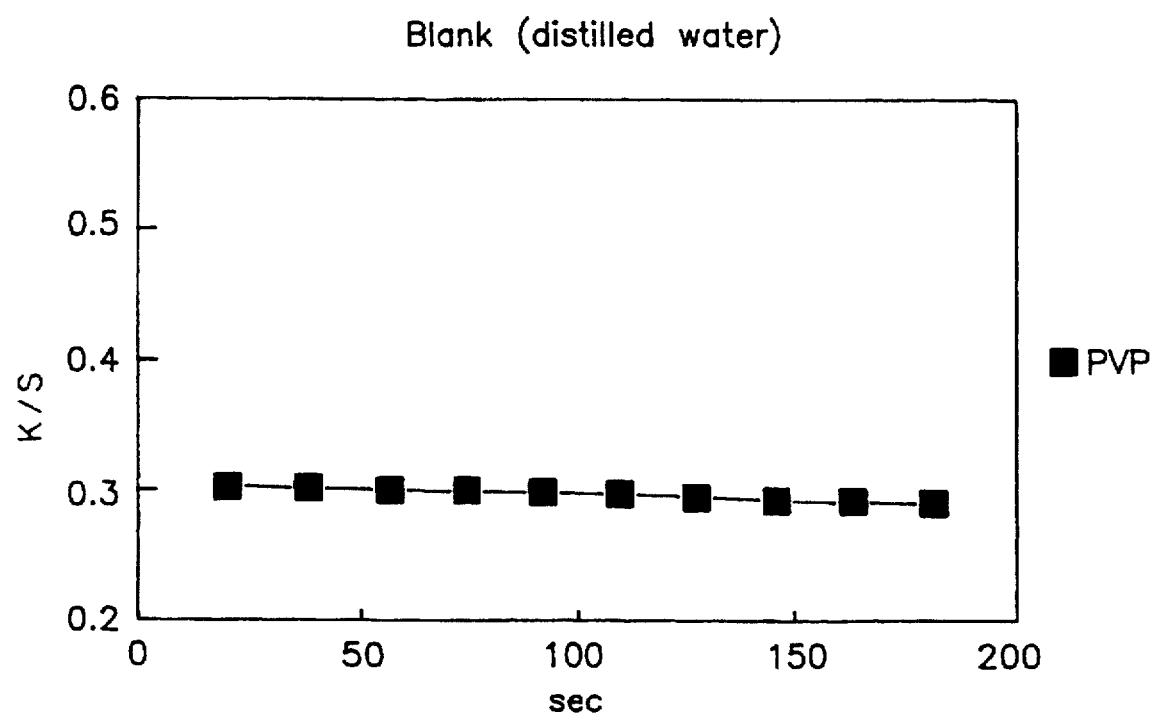
FIG. 1 is a graph showing the results in Example 1.

When the test samples are urine, they have large variety of pH values depending on individuals as explained above. Thus, it is necessary to use a buffer which has the buffering ability in a pH range between 4 and 10. The present invention uses a mixed buffer of piperazine and glycylglycine.

The water-soluble polymers are preferably water-soluble synthetic polymers and water-soluble fermentation viscous materials such as polyvinylpyrrolidone and pullulan. The use of the water-soluble synthetic polymers or fermentation viscous materials can solve the background coloring problem which may be caused by color development of thio-NAD (or thio-NADH).

The kind of sugar alcohols is not limited. If no sugar alcohol is used, the desulfatase makes the solution turbid in the preparation step, and the storage stability of the composition in the test element decreases significantly.

Examples of the sugar alcohol are D-sorbitol, D-mannitol, and the like. Compounds having similar structures to the sugar alcohols, for example, polyols such as sucrose, glycerol and polyethylene glycol may be used.

$Mn^{2+}$ ions are supplied from manganese salts. The manganese salts are preferably water-soluble salts such as manganese chloride, manganese nitrate, manganese sulfate, manganese phosphate, manganese borate, manganese acetate, and the like.

The above mixed buffer of piperazine and glycylglycine is used when the samples are urine. For test samples other than urine, any conventional buffer can be used. Of course, the mixed buffer of piperazine and glycylglycine can buffer pH of the samples other than urine.

The quantitative relationships among BSS, 3β-HSD, NADH, thio-NAD$^+$, the water-soluble polymer, sugar alcohol or $Mn^{2+}$ and buffer are as follows:

BSS: 20–200 U/ml, preferably 50–100 U/ml

3β-HSD: 5–100 U/ml, preferably 20–40 U/ml

NADH: 0.5–5 mM, preferably 2–3 mM thio-NAD$^+$: 1–5 mM, preferably 1.5–3 mM

Water-soluble polymer: 6–12% (w/w), preferably 8–10% (w/w)

Sugar alcohol: 1–5% (w/w), preferably 2–3% (w/w)

Manganese: 30–300 µM, preferably 50–150 µM

Buffer: 100–500 mM, preferably 200–300 mM

The support member can be made of any suitable material. Preferred examples of the material are polyethylene terephthalate (PET), polycarbonate, polystyrene, cellulose esters, and the like. Any film- or sheet-form polymer that is conventionally used in this type of analytical elements may be used.

The reagent layer is formed by applying a solution containing reagents onto the support member and drying it. Alternatively, a suitable substrate (e.g. filter paper, non-woven fabric, woven fabric, knit, glass fiber filter paper, etc.) is dipped in or coated with the solution and dried, and the reagent layer is obtained.

The porous developing layer is made of any material having a three-dimensional lattice structure which is conventionally used for this type of the analytical element, for example, filter paper, non-woven fabric, woven fabric, knit, glass fiber filter paper, membrane filter, polymer microbeads, and the like.

An example of the method for producing the integral multi-layer analytical element of the present invention will be explained.

BSS which is necessary for desulfation, and 3β-HSD, thio-NAD$^+$ and NADH which are necessary for the enzymatic cycling reaction are dissolved in the buffer. The formation of turbidity in the solution can be suppressed by the addition of at least one of the sugar alcohols and Mn$^{2+}$ to the buffer solution.

A solution of the water-soluble polymer dissolved in the same buffer as used above is mixed with the above enzyme solution and stirred thoroughly. The solution mixture is uniformly spread over the support member and dried, and thus the reagent layer is formed. After that, the developing layer is laminated on the reagent layer and further dried. The undesired color may develop during the two step drying and the level of background may increase. The use of high purity polyvinylpyrrolidone and/or pullulan can suppress the increase of background.

The obtained analytical element sheet is cut and adhered to a support strip with an adhesive tape, followed by cutting, and the analytical elements are obtained.

EFFECTS OF THE INVENTION

The present invention can suppress the increase of background, and prevent the agglomeration of the enzyme during the preparation of the solution in the step for forming the reagent layer.

EXAMPLES

Example 1

| Preparation of analytical element: | |
|---|---|
| Formulation | 1.33 mkat/l |
| BSS | |
| (manufactured by MARUKIN SHOYU Co., Ltd.) | (80 U/ml) |
| 3β-HSD | 0.33 mkat/l |
| (manufactured by MARUKIN SHOYU Co., Ltd.) | (20 U/ml) |
| NADH | 3.0 mmol/l |
| (manufactured by ORIENTAL ENZYMES Co., Ltd.) | |
| Thio-NAD+ | 3.0 mmol/l |
| (manufactured by ORIENTAL ENZYMES Co., Ltd.) | |
| Tween 20 | 0.5 wt. % |
| (available from NACALAI TESQUE) | |

| -continued | |
|---|---|
| Binder (polyvinylpyrrolidone) | 9.0 wt. % |
| (Kollidon 90 F manufactured by BASF) | |
| Buffer: piperazine-glycylglycine (pH 7.0) | 200 mmol/l |
| (Piperazine available from WAKO JUNYAKU Co., Ltd. and glycylglycine available from NACALAI TESQUE in a molar ratio of 1:1) | |
| D-Sorbitol | 3.0% |
| (available from NACALAI TESQUE) | |

[Based on the whole weight of the coating liquid]

The above components were mixed, and the obtained solution was coated on the surface of a PET film and dried at 40° C. for about 10 minutes.

A piece of filter paper in which 0.01% Triton X-100 had been impregnated was placed on the above dried layer and press adhered, and a developing layer was laminated. Then, the laminated layers were dried, and a test element sheet was obtained.

A double coated adhesive tape was adhered to the PET side of the element sheet and cut to the determined size. The cut element was adhered to a support strip of PET and an analytical element strip was obtained.

Measurement:

Each analytical element was subjected to the test using lithocholilglycine 3-sulfate (hereinafter referred to as "GLCA") as a component to be analyzed, and the change rate of a reflectance after 110 seconds was measured with a specially designed reflectometer ("SPOTCHEM" manufactured by KYOTO DAIICHI KAGAKU Co., Ltd.).

The unit "K/S", which was used in Table 1, is a unit used for converting the reflectance to a concentration, and expressed by the formula:

$$K/S=(1-R)^2/2R$$

in which R is a reflectance.

The K/S value increases as the concentration of a component to be analyzed increases in the test sample, while this value decreases and the concentration decreases.

The results in Example 1 are shown in Table 1.

TABLE 1

| | GLCA concentration (µmol/l) | | |
|---|---|---|---|
| | 0 | 10 | 100 |
| Example 1 | 0.298 | 0.532 | 1.112 |

(Units: K/S)

Sufficient sensitivities were attained in proportion to the GLCA concentrations in Example 1, since the level of background decreased.

The change of blank values over time is shown in the graph of FIG. 1. It is understood that the K/S values were stabilized. "PVP" in the graph stands for polyvinylpyrrolidone.

Example 2

Urine samples (each 5 µl), which contained 10 µmol/l of GLCA and pH of which had been adjusted to the values in Table 2 with 1N hydrochloric acid or 1N aqueous sodium hydroxide, were spotted on the respective analytical element.

pH of the spotted urine samples was monitored with a compact pH meter. The results are shown in Table 2.

TABLE 2

| pH of urine | 4.3 | 5.3 | 6.0 | 7.2 | 8.6 |
|---|---|---|---|---|---|
| Measured pH | 6.7 | 6.8 | 6.9 | 6.9 | 6.9 |

These results indicate that the composition of the present invention has the sufficient buffering properties for the urine samples having pH in a wide range.

What is claimed is:

1. An integral multi-layer analytical element for analyzing bile acid sulfate comprising a support member, a reagent layer on said support member and a porous developing layer on said reagent layer, at least one of said reagent layer and said developing layer containing bile acid sulfate sulfatase, 3β-hydroxysteroid dehydrogenase and a combination of thio-NAD$^+$ and reduced NADs or reduced NADPs, wherein said reagent layer contains a water-soluble polymer, a buffer and at least one component selected from the group consisting of sugar alcohols and Mn$^{2+}$.

2. An integral multi-layer analytical element for analyzing bile acid sulfate according to claim 1, wherein said water-soluble polymer is selected from water-soluble synthetic polymers and water-soluble fermentation viscous materials.

3. An integral multi-layer analytical element for analyzing bile acid sulfate according to claim 1 or 2, wherein said buffer contained in said reagent layer is a buffer having the buffering properties in the pH range between 4 and 10.

4. An integral multi-layer analytical element for analyzing bile acid sulfate according to claim 3, wherein said buffer is a mixed buffer of piperazine and glycylglycin.

5. An integral multi-layer analytical element for analyzing bile acid sulfate according to claim 1, wherein at least one of said reagent layer and said developing layer contains 20–200 U/ml of bile acid sulfate sulfatase, 5–100 U/ml of 3β-hydroxysteroid dehydrogenase, 0.5–5 mM of thio-NAD$^+$ and reduced NAD, or reduced NADP, 1–5 mM of thio-NAD$^+$, 6–12% (w/w) of the water-soluble polymer, 100–500 mM of the buffer, 1–5% (w/w) of the sugar alcohols and 30–300 μM of Mn$^{2+}$.

* * * * *